US011612486B2

(12) United States Patent
Mommaerts

(10) Patent No.: US 11,612,486 B2
(45) Date of Patent: Mar. 28, 2023

(54) BONE PROSTHESIS AND METHOD FOR ITS PLACEMENT

(71) Applicant: CADSKILLS BVBA, St. Martens-Latem (BE)

(72) Inventor: Maurice Yves Mommaerts, St. Martens-Latem (BE)

(73) Assignee: CADSKILLS BVBA, St. Martens-Latem (BE)

( * ) Notice: Subject to any disclaimer, the term of this patent is extended or adjusted under 35 U.S.C. 154(b) by 511 days.

(21) Appl. No.: 16/496,658

(22) PCT Filed: Mar. 23, 2018

(86) PCT No.: PCT/IB2018/051968
§ 371 (c)(1),
(2) Date: Sep. 23, 2019

(87) PCT Pub. No.: WO2018/172982
PCT Pub. Date: Sep. 27, 2018

(65) Prior Publication Data
US 2020/0375747 A1    Dec. 3, 2020

(30) Foreign Application Priority Data

Mar. 23, 2017    (NL) .................................... 1042314

(51) Int. Cl.
*A61F 2/30* (2006.01)
*A61F 2/46* (2006.01)

(52) U.S. Cl.
CPC ........ *A61F 2/3099* (2013.01); *A61F 2/30942* (2013.01); *A61F 2002/30011* (2013.01);
(Continued)

(58) Field of Classification Search
CPC ................ A61F 2/30988; A61F 2/3099; A61F 2002/30991; A61F 2002/30993;
(Continued)

(56) References Cited

U.S. PATENT DOCUMENTS 3,683,422 A     8/1972   Stemmer et al.
4,355,427 A  * 10/1982   Schneider ................. A61F 2/40
                                                             606/62
(Continued)

FOREIGN PATENT DOCUMENTS

CN        101 642 393       2/2010
CN        103 479 450       1/2014

OTHER PUBLICATIONS

International Search Report, PCT/IB2018/051968, dated Jul. 9, 2018.
Written Opinion, PCT/IB2018/051968, dated Jul. 9, 2018.

*Primary Examiner* — Alvin J Stewart
(74) *Attorney, Agent, or Firm* — Nixon & Vanderhye

(57) ABSTRACT

A prosthesis for at least a portion of a bone, in particular a bone or portion thereof to which, in the natural condition, a tendon of a muscle is attached, wherein the prosthesis is manufactured of a metal or an alloy thereof and is provided with at least one area situated in the surface of the prosthesis that faces outward once the prosthesis has been placed in the body, the area being formed by a layer provided with open spaces that are connected to each other, wherein the open spaces are dimensioned for allowing the growth of bone tissue therein.

18 Claims, 3 Drawing Sheets

(52) U.S. Cl.
CPC ............... *A61F 2002/3092* (2013.01); *A61F 2002/3093* (2013.01); *A61F 2002/30322* (2013.01); *A61F 2002/30688* (2013.01); *A61F 2002/30962* (2013.01); *A61F 2002/30985* (2013.01); *A61F 2002/30991* (2013.01); *A61F 2002/4616* (2013.01)

(58) Field of Classification Search
CPC .... A61F 2002/3092; A61F 2002/30929; A61F 2002/3093; A61F 2/30767; A61F 2002/30769; A61F 2002/4616; A61F 2002/30688
See application file for complete search history.

(56) References Cited

U.S. PATENT DOCUMENTS

| | | | | |
|---|---|---|---|---|
| 4,502,161 A * | 3/1985 | Wall | ............ | A61F 2/3872 623/14.12 |
| 4,608,052 A * | 8/1986 | Van Kampen | ...... | A61F 2/30771 623/23.29 |
| 4,636,215 A * | 1/1987 | Schwartz | ............ | A61F 2/2803 606/76 |
| 4,778,472 A * | 10/1988 | Homsy | ............ | A61F 2/30965 623/17.17 |
| 4,919,668 A * | 4/1990 | Rosenbaum | ......... | A61F 2/3099 623/17.17 |
| 4,936,852 A * | 6/1990 | Kent | ............ | A61F 2/30767 623/17.17 |
| 5,489,305 A * | 2/1996 | Morgan | ............ | A61B 17/8071 623/17.17 |
| 5,549,680 A * | 8/1996 | Gordon | ............ | A61F 2/3099 623/17.17 |
| 6,398,812 B1 * | 6/2002 | Masini | ............ | A61F 2/4059 623/19.11 |
| 6,406,496 B1 * | 6/2002 | Ruter | ............ | A61F 2/4059 623/19.11 |
| 6,899,736 B1 * | 5/2005 | Rauscher | ............ | A61F 2/40 623/19.12 |
| 7,070,622 B1 * | 7/2006 | Brown | ............ | A61F 2/40 623/20.14 |
| 7,175,664 B1 * | 2/2007 | Lakin | ............ | A61F 2/36 623/19.14 |
| 7,556,652 B2 * | 7/2009 | Angibaud | ............ | A61F 2/4059 623/19.14 |
| 8,118,868 B2 * | 2/2012 | May | ............ | A61F 2/367 623/13.14 |
| 8,177,849 B2 * | 5/2012 | Meyers | ............ | A61F 2/3607 623/20.32 |
| 8,182,542 B2 * | 5/2012 | Ferko | ............ | A61F 2/0811 623/19.14 |
| 8,226,725 B2 * | 7/2012 | Ferko | ............ | A61F 2/3877 623/20.14 |
| 8,308,806 B2 * | 11/2012 | Grant | ............ | A61F 2/40 623/19.14 |
| 8,579,984 B2 * | 11/2013 | Borowsky | ............ | A61F 2/4014 623/19.14 |
| 8,715,356 B2 * | 5/2014 | Porter | ............ | A61F 2/40 623/19.14 |
| 8,979,940 B2 * | 3/2015 | Porter | ............ | A61F 2/32 623/23.15 |
| 9,345,580 B2 * | 5/2016 | Porter | ............ | A61F 2/3804 |
| 9,833,326 B2 * | 12/2017 | Porter | ............ | A61F 2/3804 |
| 10,251,744 B2 * | 4/2019 | Treacy | ............ | A61B 17/842 |
| 10,765,524 B2 * | 9/2020 | Boileau | ............ | A61F 2/4014 |
| 11,000,360 B2 * | 5/2021 | D'Agostino | ............ | A61F 2/34 |
| 2003/0074081 A1 | 4/2003 | Ayers | | |
| 2004/0107594 A1 * | 6/2004 | Afriat | ............ | A61F 2/30942 33/562 |
| 2005/0273165 A1 * | 12/2005 | Griffiths | ............ | A61F 2/2803 623/16.11 |
| 2007/0156246 A1 * | 7/2007 | Meswania | ............ | A61F 2/40 623/19.12 |
| 2007/0244565 A1 * | 10/2007 | Stchur | ............ | A61F 2/4059 623/19.14 |
| 2007/0288020 A1 * | 12/2007 | Yang | ............ | A61F 2/0811 606/279 |
| 2008/0004711 A1 * | 1/2008 | Li | ............ | A61B 17/86 623/23.22 |
| 2008/0281428 A1 * | 11/2008 | Meyers | ............ | A61F 2/3607 623/20.35 |
| 2008/0288083 A1 * | 11/2008 | Axelsson | ............ | A61F 2/30907 623/23.51 |
| 2011/0130840 A1 * | 6/2011 | Oskouei | ............ | A61F 2/30721 623/18.11 |
| 2012/0035733 A1 * | 2/2012 | Porter | ............ | A61F 2/3804 623/18.11 |
| 2012/0089143 A1 * | 4/2012 | Martin | ............ | A61B 17/0469 606/62 |
| 2012/0101583 A1 * | 4/2012 | Lascar | ............ | A61F 2/40 623/19.14 |
| 2012/0209390 A1 | 8/2012 | Gosset et al. | | |
| 2013/0030529 A1 * | 1/2013 | Hunt | ............ | A61F 2/30771 623/16.11 |
| 2013/0030540 A1 * | 1/2013 | Leibinger | ............ | A61F 2/28 29/505 |
| 2013/0131699 A1 | 5/2013 | Jiang et al. | | |
| 2016/0081806 A1 * | 3/2016 | Dubois | ............ | A61F 2/3099 623/17.17 |
| 2018/0055643 A1 * | 3/2018 | Castro | ............ | A61L 27/58 |
| 2018/0193530 A1 * | 7/2018 | Barbas | ............ | A61F 2/2875 |
| 2018/0214261 A1 * | 8/2018 | Treacy | ............ | A61F 2/28 |
| 2019/0192302 A1 * | 6/2019 | Mommaerts | ............ | A61F 2/3099 |
| 2020/0129296 A1 * | 4/2020 | Chary | ............ | A61F 2/30 |

* cited by examiner

BONE PROSTHESIS AND METHOD FOR ITS PLACEMENT

BACKGROUND OF THE INVENTION

The invention relates to a prosthesis for at least a portion of a bone of a body, in particular a human body, in particular a bone or portion thereof to which in the natural condition a tendon of a muscle is attached.

When a (portion of a) bone that may or may not be part of a joint, needs to be replaced by a prosthesis, this also means that if the bone portion in question is also the location of attachment of a tendon of a muscle, this tendon has to be detached therefrom. Once the prosthesis has been placed, there will be too little possibility for anchoring the tendon. After all, a large part of the bone has then been replaced by the prosthesis to which a tendon is unable to attach biologically. Often, prostheses are manufactured of metals such as titanium or alloys thereof.

Under certain circumstances it may be possible to secure the tendon in question to bone at a different location. However, this involves the drawback of the play of forces being different from the natural one.

Therefore, it is often decided not to reattach said tendon, rendering the muscle in question idle. Another muscle seldom is capable of taking over the function, and if so only to a limited extent. This may cause the patient great inconvenience.

Take for instance the mandible, in case on one side thereof the condylar head of the temporomandibular joint has to be replaced by a prosthesis. The condylar head constitutes the location of attachment for the lower branch of the lateral pterygoid muscle, which muscle ensures that the mouth can open and the discus articularis can shift in ventral direction. The one-sided or double-sided unavailability of this muscle function can cause the patient great trouble when chewing and speaking. Furthermore, the absence of the muscle function in the face may be visible to others as the chin goes lopsided when opening the mouth.

SUMMARY OF THE INVENTION

It is an object of the invention to provide a bone prosthesis with which once it has been placed in the body, the activity of a muscle that was originally connected to the replaced bone (portion) can be preserved.

According to one aspect, the invention provides a prosthesis for at least a portion of a bone of a body, in particular a bone or portion thereof to which in the natural condition a tendon of a muscle is attached, wherein the prosthesis is manufactured of a metal or an alloy thereof and is provided with at least one area situated in the surface of the prosthesis that faces outward once the prosthesis has been placed in the body, said area being formed by a layer of material provided with open spaces that are connected to each other.

On the porous surface thus provided a tendon can be placed, in engagement therewith. The layer provided with interconnected spaces, pores, which is situated at the (outer) surface of the prosthesis forms a bed, as it were, in which bone tissue can develop. Interstitial tissue fibers of the tendon can grow into the said bone tissue.

The interconnected spaces form an open structure which, when filled with bone tissue, provide an anchoring action, in particular due to the fact that the material of the said area extends over many open spaces. In that way an attachment possibility is provided to tendon tissue, which would otherwise not be able to attach to the prosthesis, in particular due to the selected material. As a result, the muscle function in question does not need to be lost.

It is also possible that if a piece of bone or bone fragment is left attached to the detached tendon, said bone fragment attaches to the newly formed bone tissue in the prosthesis pores due to bone healing.

The said area with a porous surface is located on the prosthesis at a location corresponding with the location of enthesis of the tendon of the muscle on the bone for which the prosthesis is a replacement.

The porous area is local, and at the outer surface of the prosthesis is surrounded by surfaces of the outer surface of the prosthesis, said surfaces being without pores, in particular smooth surfaces.

In one embodiment, which has a large degree of porosity, the layer is formed by ribs, bars or small rods of the material of the said layer, having the appearance of a spatial skeleton or three-dimensional grid, wherein the spaces between the ribs, bars or small rods are open.

In an alternative embodiment, the open spaces are formed by a crisscross system of short channels that are in open connection with each other, each bounded by the material of the layer. The little channels may extend in various directions. The little channels may extend in a direction having a directional component that is parallel to the tangent plane on the nearest outer surface of the said area.

The structure defining open spaces, in particular grid, may be regular.

The size of the cross-section of the open spaces, pores, open cells, may be in the range of 0.25 mm-1.0 mm, more in particular in the range of 0.35 mm and 1.0 mm, more in particular between more than 0.41 mm and 1.0 mm.

In order to promote the development of bone tissue, the open spaces may have a cross-section in the range of 0.45 mm-0.55 mm. The open spaces may have a mutually at least almost equal cross-section.

The anchoring of the tendon via the bone tissue is promoted if the layer provided with open spaces is at least approximately 0.5 mm thick, preferably a few mm thick.

The layer provided with open spaces may have a porosity in the range of approximately 50%-approximately 95%.

The area of the layer with open spaces may have such dimensions and such a shape in the surface of the prosthesis, that it will be possible for it to be entirely covered by the tendon.

In case several muscles were connected to the replaced bone (portion), there may be several areas on the prosthesis that are surrounded by surfaces without pores, in particular smooth surfaces. A potential attachment area will then be available to each tendon.

The said layer may be manufactured of the same material as the adjacent areas of the prosthesis. The prosthesis can be formed as one unity. Alternatively, the prosthesis may be manufactured in several parts that are fixedly attached to each other.

The said layer, optionally the entire prosthesis, may be manufactured by means of a process of additive production technique, such as stereolithography, FDM, SLM, SLS or another 3D printing technique. In that way any desired open structure, be it regular or irregular, can be manufactured.

The said layer, optionally the entire prosthesis, may be manufactured of titanium or an alloy thereof. The presence of titanium oxide on the surface of the material of the layer, such as on the ribs, may be conducive to the development of bone tissue. It may have been formed there due to titanium being exposed to air. Another bone growth stimulating coating, such as a type of calcium phosphate, may have been applied using a suitable application technique.

In or in the proximity of the said area, the prosthesis may be provided with an accommodation space for a suture, loop, hook, clamp or other device for at least initially securing the tendon in engagement with the said area. This may for instance be a tunnel extending through the prosthesis, or a groove running the perimeter of the prosthesis. The tunnel or groove can be used for the accommodation of a suture to be used for the tendon. The suture or another added (temporary) attachment means will become defunct once the tendon has sufficiently attached itself to the bone tissue.

The prosthesis itself may for instance be attached to the natural (healthy) bone using bone screws, and for that purpose be provided with holes for bone screws.

To accelerate the attachment process of the tendon, the formation of bone tissue in the open spaces, pores, open cells can be promoted by applying a growth factor promoting the production of bone tissue therein. The growth factor may be a protein selected from the group consisting of PDGF, IGF, TGF-β, BMP, FGF, VEGF and PRP. In the open spaces, stem cells can also be placed or allowed in, or autologous/heterologous bone transplants can be disposed.

According to one embodiment, the invention can be used as prosthesis for the mandibular side of a temporomandibular joint. In particular such a prosthesis may comprises a head part to replace the condylar head as well as an attachment plate for attaching the prosthesis to the ascending branch of the mandible, and a condylar neck connecting them to each other, wherein the condylar neck is provided with one or more of the aforementioned areas. This area may be situated such that it is suitable for attachment of the tendon to at least one branch of the lateral pterygoid muscle, preferably both branches of said muscle. For that purpose, said area may be provided on the antero-medial side of the condylar neck.

For said purpose of securing the tendon temporarily, the prosthesis may be provided with a groove or a passage for a suture, in particular in the condylar neck.

Other applications are possible, in particular for other joints.

According to a further aspect, the invention provides a method for arranging a prosthesis for at least a portion of a bone, in particular a bone or portion thereof to which in the natural condition a tendon of a muscle is attached, wherein the prosthesis is manufactured of a metal or an alloy thereof and is provided with at least one porous area situated in the surface of the prosthesis that faces outward once the prosthesis has been placed in the body, said area being formed by a layer of material provided with open spaces that are connected to each other, comprising the following steps:

a—detaching one or more tendons, with or without their original enthesis in a bone fragment, from the bone area to be replaced and removing the bone area to be replaced;
b—positioning the prosthesis at the wanted location to replace the said bone area;
c—at least temporarily securing the tendons, with or without their original enthesis in a bone fragment, on the prosthesis, in engagement with the porous areas; and
d—promoting the formation of bone tissue in the said area, inside the layer, and allowing the interstitial tissue fibers of the tendon to grow into the bone tissue formed in the pores of the said area of the prosthesis, or through bone healing allowing the bone fragment to attach to the bone tissue formed in the pores in the said area of the prosthesis.

In one embodiment, prior to step b) being carried out, the open spaces are provided with a growth factor promoting the production of bone tissue.

In one embodiment, prior to step b) being carried out, stem cells are introduced into the open spaces.

In another embodiment, stem cells are allowed in after step c), in particular in a natural post-surgery process.

In one embodiment, wherein said prosthesis for the condylar head is placed, in step a) the at least one branch of the lateral pterygoid muscle, with or without original enthesis including bone fragment, is detached from the bone area to be replaced, and wherein in step c) the branch in question of the lateral pterygoid muscle, with or without original enthesis including bone fragment, is secured to the prosthesis, on the porous area on the antero-medial side of the condylar neck. In one embodiment the steps a) and c) are carried out for the lower branch of the lateral pterygoid muscle.

According to a further aspect, the invention provides a method for preparing the arrangement of a bone prosthesis in a body to replace a portion of a bone to which a tendon is attached, comprising the following steps:

a—identifying, such as by scanning, the bone portion (location, size, shape) that is to be replaced by the prosthesis and identifying the location of the attachment/enthesis of the tendon;
b—based on the outcome of step a) designing the prosthesis, with a discrete porous area that debouches in the surface of the prosthesis, the area corresponding with the location of attachment/enthesis of the tendon as identified in step a);
c—manufacturing the prosthesis in accordance with the design made in step b).

Here, the prosthesis can be manufactured according to one or more of the embodiments of the prosthesis according to the invention as described above.

The aspects and measures described in this description and the claims of the application and/or shown in the drawings of this application may where possible also be used individually. Said individual aspects may be the subject of divisional patent applications relating thereto. This particularly applies to the measures and aspects that are described per se in the sub claims.

BRIEF DESCRIPTION OF THE DRAWINGS

The invention will be elucidated on the basis of a number of exemplary embodiments shown in the attached drawings, in which.

DETAILED DESCRIPTION OF THE DRAWINGS

Figure 1B:
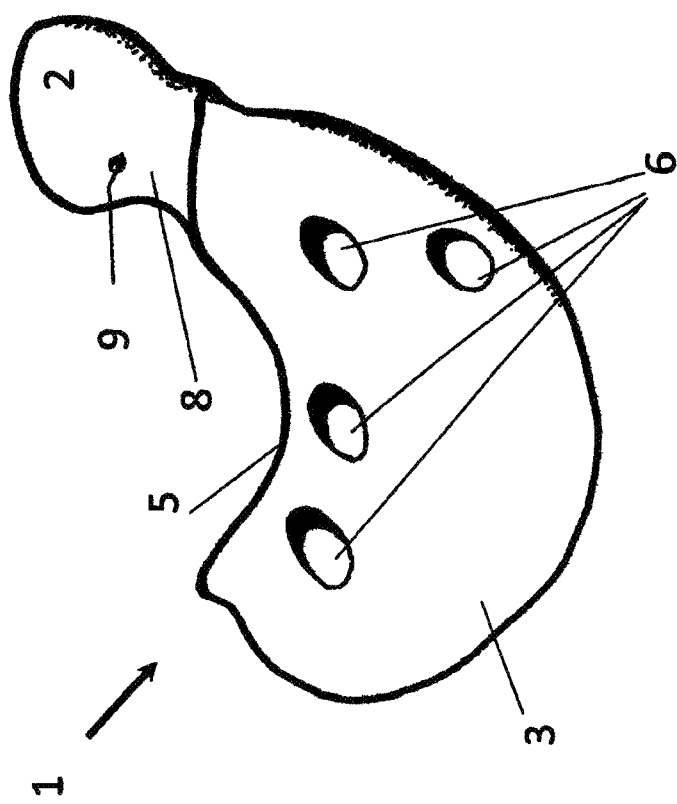
FIGS. 1A and 1B show a second first exemplary embodiment of a prosthesis according to the invention.
Figure 1A:
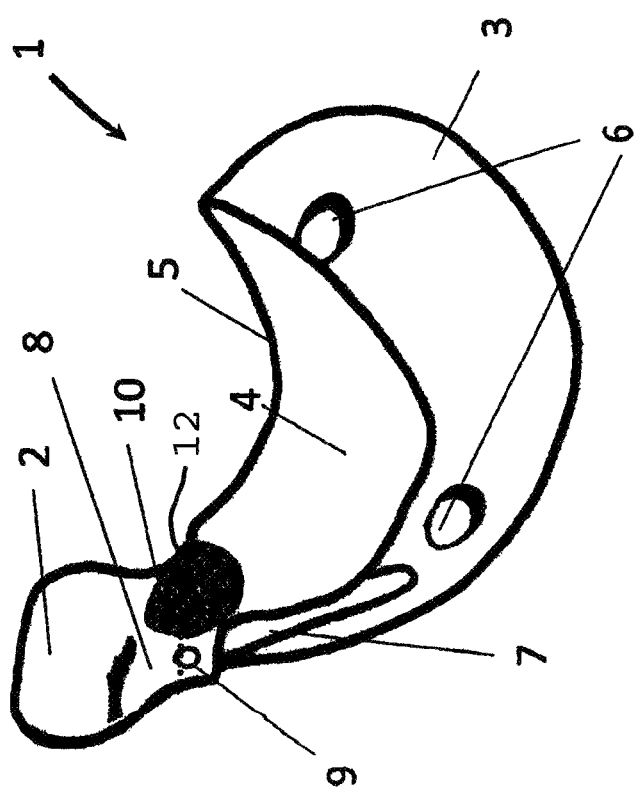
Figure 2A:
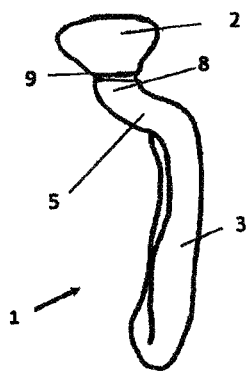
FIGS. 2A-D show a second exemplary embodiment of a prosthesis according to the invention.
Figure 2B:
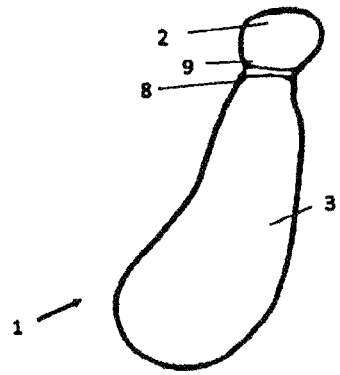
Figure 2C:
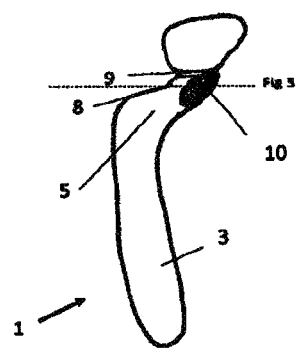
Figure 2D:
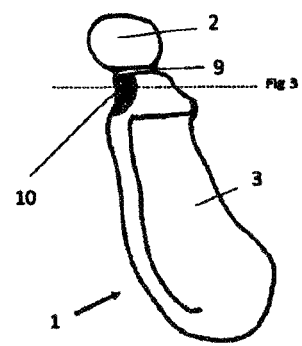

FIGS. 1A and 1B show the mandibular component 1 of a temporomandibular joint prosthesis (TMJ prosthesis), which comprises a lateral wing 3 and a medial wing 4, that are connected to each other by an upper portion or ridge 5 forming one unity therewith, so that a kind of saddle shape is achieved. The lateral wing 3 is provided with bone screw holes 6.

At the rear end via a neck 8, an artificial condylar head 2 projects upwards, like a kind of saddle horn or pommel. As can be seen in FIG. 1A a downwardly extending pin 7 is provided within the component 1 at the rear end, which pin remains spaced apart from both wings 3 and 4. Said pin 7 is optional and may be provided as intramedullary pin.

A through hole 9 running from the lateral side to the medial side is provided in the neck 8, which hole is suitable for passing a surgical suture through.

The mandibular component 1 is designed and manufactured in correspondence with the shape and condition of the ascending branch of the mandible of the patient in question, such that both wings fittingly abut the ascending branch of the maxilla, wherein the artificial condylar head 2 replaces the condylar head, and the upper portion 5 fittingly abuts the upper edge of the incisura semilunaris.

In the area of the neck 8, in its outer surface, an area 10 is furthermore provided, which contrary to the adjacent solid areas having a smooth surface, forms a porous surface 12. This area 10 is situated on the antero-medial side of the condylar neck 8 and has a surface which in terms of size and shape is adapted to the dimensions of the portion of the tendon of the muscle in question to be attached thereto. The area 10 may have a thickness of for instance 1 mm and constitutes the porous surface of a layer of material having an open structure. The size of the cross-sections of the open spaces in the porous area in this example is 0.45 to 0.55 mm.

FIGS. 2A-D show an alternative, simpler embodiment of the mandibular component 1 of a temporomandibular joint prosthesis (TMJ prosthesis), from four different sides. The component 1 now comprises a lateral wing 3, a shoulder 5 and a condylar head 2, which are connected to each other by a condylar neck 8. A groove 9 for a suture runs the perimeter of the neck 8. In this example as well, an area 10 is situated on the antero-medial side of the condylar neck 8, which area contrary to the adjacent areas with a smooth surface, forms a porous area. Screw holes in the wing 3 have been left out here.

In this example, the mandibular component 1 is manufactured as one unity of titanium, by means of a 3D printing technique, geared to the patient in question.

Figure 3:
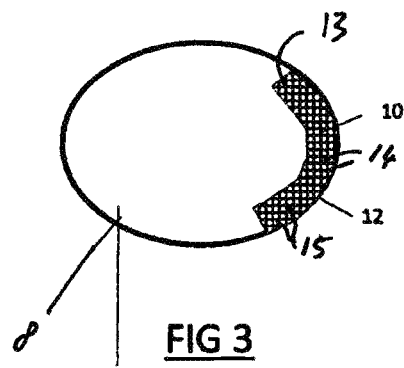
FIG. 3 shows a schematic cross-section according to arrow 3 in FIGS. 2A-D.

In FIG. 3 a highly schematic cross-section of an area 10 is shown, with adjacent thereto the solid areas of the prosthesis. The area 10, providing a porous surface 12 with openings 11, is formed by a layer 13 which is built up from a regular system of bars 14 and has an open structure. The bars 14 form a spatial skeleton, also called scaffold, having open spaces or pores 15 in there that are connected to each other and to the openings 11. The bars 14 may bound passages that each time have a smallest cross-section of approximately 0.5 mm. The thickness of the area 10 is 2 mm here. The area 10 is manufactured of titanium together with the prosthesis as one unity, using the aforementioned 3D printing technique. In the course time, under the influence of air, titanium oxide will be formed on the surface of the bars 14. In this example, the surface adjacent to the porous area 10 is smooth.

Prior to the operation in which the mandibular component and the related fossa component that is not shown, are placed, stem cells and/or growth factors are applied in the open spaces 15, in this case on the bars 14.

Figure 4:
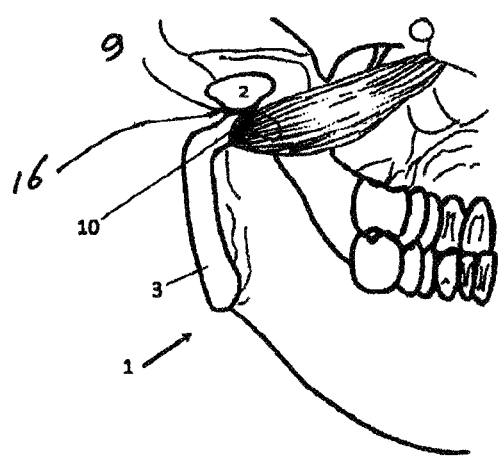
FIG. 4 shows a schematic representation of a prosthesis according to FIGS. 2A-D in a condition in which it is placed on a mandible.

During the operation to/in the body of a patient, also see FIG. 4, once access to the area of surgery has been obtained, both branches of the lateral pterygoid muscle are detached from the natural, diseased condylar head to be replaced. The other ends of these muscles remain attached to the infratemporal surface and tip of the greater wing of the sphenoid bone (for the upper branch) and the lateral surface of the lateral pterygoid plate (for the lower branch), respectively.

Once the parts to be replaced have been removed and the contact surfaces of the jaw have been prepared, the mandibular component 1 can be placed with the shoulder 5 on the upper edge of the bone, and using bone screws, the prosthesis can be secured with the wing 3 against the lateral side of the healthy bone. The area 10 is exposed and is available for placing the tendon of the lateral pterygoid muscle detached earlier against it. With a suture 16 placed in the groove 9, see FIG. 4, this contact is at least temporarily secured.

Once the fossa component has also been placed and further actions have been carried out to carry the surgery through, bone tissue will be formed in the open spaces 15, which fills the open spaces 15 and at the exterior of area 10 contacts the tendon held against it. Interstitial tissue fibers of the tendon will penetrate the bone tissue formed in the pores as a result of which an intimate connection between bone tissue and tendon and therefore the muscle is realized. The bone tissue filling the open spaces between the bars 14 forms an anchoring of said connection. The suture will then become defunct.

Use is thus made of the insight that the formation of bone tissue can also be useful on surfaces of a prosthesis that are not in contact with a bone: in this case for the formation of a connection between tendon and prosthesis, in addition to forming an anchoring. The anchoring is promoted because the material of the said area extends over a large number of open spaces, or in other words, (parts of) initially hollow spaces, that are now filled with bone tissue, are covered to the outside by that material. The bone tissue formed, forms a spatial structure in the interconnected hollow spaces situated within the (initially) spatial structure of the material of the porous layer.

It is also possible to use the prosthesis according to the invention if an end of a tendon with the enthesis including a bone part (bone fragment) of the bone to be replaced is detached and once the prosthesis has been placed, allowing said bone fragment to connect to the bone tissue formed in the pores through bone healing. The said bone fragment contains collagen of the tendon, which can be favorable to the insertion. In this embodiment, the presence of the bone part (bone fragment) can be taken into account in the design of the prosthesis, in particular the porous area.

The invention is/inventions are not at all limited to the embodiments discussed in the description and shown in the drawings. The above description has been included to illustrate the operation of preferred embodiments of the invention and not to limit the scope of the invention. Starting from the above explanation many variations that fall within the spirit and scope of the present invention will be evident to an expert. Variations of the parts described in the description and shown in the drawings are possible. They can be used individually in other embodiments of the invention(s). Parts of the various examples given can be combined together.

The invention claimed is:

1. A prosthesis for at least a portion of a bone of a body, in particular a bone or portion thereof to which in the natural condition a tendon of a muscle is attached, wherein the prosthesis is manufactured of a metal or of an alloy thereof and is provided with at least one area situated in the surface of the prosthesis that faces outward once the prosthesis has been placed in the body, said area being formed by a layer of material provided with open spaces that are connected to each other so as to form a porous area, wherein the open spaces are dimensioned for allowing the growth of bone tissue therein, and wherein the porous area is a local area at the outer surface of the prosthesis, the local area being surrounded by surfaces of the outer surface of the prosthesis, said surfaces being without pores and being smooth surfaces, wherein the prosthesis is designed as prosthesis for the mandibular side of a temporomandibular joint.

2. The prosthesis according to claim 1, wherein the open spaces in the porous area are formed by a crisscross system of short channels that are in open connection with each other, each bounded by the material of the layer.

3. The prosthesis according to claim 1, wherein the size of the cross-section of the open spaces is in the range of 0.35 mm-1.0 mm, more in particular between more than 0.41 mm and 1.0 mm.

4. The prosthesis according to claim 1, wherein the said porous area has a porous surface which is located on the prosthesis at a location corresponding with the location of enthesis of the tendon of the muscle on the bone for which the prosthesis constitutes a replacement.

5. The prosthesis according to claim 1, wherein the layer with the porous area, optionally the entire prosthesis, is manufactured of titanium or an alloy thereof.

6. The prosthesis according to claim 1, in or in the proximity of the said porous area provided with an accommodation space for a suture, clamp or other device for at least initially securing the tendon in engagement with the porous area.

7. The prosthesis according to claim 1, wherein the open spaces are provided with a growth factor promoting the production of bone tissue.

8. The prosthesis according to claim 1, wherein at least said layer is manufactured by means of a process of additive production technique, such as stereolithography, FDM, SLM, SLS or another 3D printing technique.

9. The prosthesis according to claim 1, comprising a head part to replace the condylar head and an attachment plate for attaching the prosthesis to the ascending branch of the lower branch, and a condylar neck connecting them to each other, wherein the condylar neck is provided with one or more of the aforementioned areas.

10. The prosthesis according to claim 9, provided with a groove or a passage for a suture, wherein, preferably, the groove or the passage is situated in the condylar neck.

11. The prosthesis according to claim 1, wherein the prosthesis is provided with holes for attachment means, such as bone screws, for attaching the prosthesis to the bone.

12. A method for arranging a prosthesis for at least a portion of a bone of a body, in particular a human body, in particular a bone or portion thereof to which in the natural condition a tendon of a muscle is attached, wherein the prosthesis is designed according to claim 1, comprising the following steps:
a-detaching tendons from the bone area to be replaced and removing the bone area to be replaced;
b-positioning the prosthesis at the wanted location;
c-at least temporarily securing the tendons on the prosthesis, in engagement with the said porous areas; and
d-promoting the formation of bone tissue in the open spaces of the porous areas and allowing the interstitial tissue fibers of the tendon to grow into the bone tissue formed in the pores of the said area of the prosthesis, the method being carried out for the arrangement of a prosthesis for at least a portion of a bone of a body, in particular a bone or portion thereof to which in the natural condition a tendon of a muscle is attached, wherein the prosthesis is manufactured of a metal or of an alloy thereof and is provided with at least one area situated in the surface of the prosthesis that faces outward once the prosthesis has been placed in the body, said area being formed by a layer of material provided with open spaces that are connected to each other, the prosthesis comprising a head part to replace the condylar head and an attachment plate for attaching the prosthesis to the ascending branch of the lower branch, and a condylar neck connecting them to each other, wherein the condylar neck is provided with one or more of the aforementioned areas wherein in step a) the at least one branch of the lateral pterygoid muscle is detached from the bone area to be replaced, and wherein in step c) the branch in question of the lateral pterygoid muscle is secured on the prosthesis, on the porous area on the antero-medial side of the condylar neck.

13. The method according to claim 12, wherein prior to step b) being carried out, the open spaces are provided with a growth factor promoting the production of bone tissue.

14. The method according to claim 12, wherein prior to step b) being carried out stem cells are introduced into the open spaces.

15. The prosthesis according to claim 1, wherein the layer provided with pores is at least approximately 0.5 mm thick, preferably a few mm thick.

16. A method for arranging a prosthesis for at least a portion of a bone of a body, in particular a human body, in particular a bone or portion thereof to which in the natural condition a tendon of a muscle is attached, wherein the prosthesis for at least a portion of a bone of a body, in particular a bone or portion thereof to which in the natural condition a tendon of a muscle is attached, wherein the prosthesis is manufactured of a metal or of an alloy thereof and is provided with at least one area situated in the surface of the prosthesis that faces outward once the prosthesis has been placed in the body, said area being formed by a layer of material provided with open spaces that are connected to each other, so as to form a porous area, wherein the open spaces are dimensioned for allowing the growth of bone tissue therein, and wherein the porous area is a local area at the outer surface of the prosthesis, the local area being surrounded by surfaces of the outer surface of the prosthesis, said surfaces being without pores and being smooth surfaces, the method comprising the following steps:
a-detaching tendons from the bone area to be replaced and removing the bone area to be replaced;
b-positioning the prosthesis at the wanted location;
c-at least temporarily securing the tendons, with their original enthesis in a bone fragment, on the prosthesis, in engagement with the said porous areas; and
d-promoting the formation of bone tissue in the open spaces of the porous areas and through bone healing allowing the bone fragment to attach to the bone tissue formed in the pores in the said area of the prosthesis, the method being carried out for the arrangement of a prosthesis for at least a portion of a bone of a body, in particular a bone or portion thereof to which in the natural condition a tendon of a muscle is attached, wherein the prosthesis is manufactured of a metal or of an alloy thereof and is provided with at least one area situated in the surface of the prosthesis that faces outward once the prosthesis has been placed in the body, said area being formed by a layer of material provided with open spaces that are connected to each other, the prosthesis comprising a head part to replace the condylar head and an attachment plate for attaching the prosthesis to the ascending branch of the lower branch, and a condylar neck connecting them to each other, wherein the condylar neck is provided with one or more of the aforementioned areas wherein in step a) the at least one branch of the lateral pterygoid muscle, with original enthesis including bone fragment, is detached from the bone area to be replaced, and wherein in step c) the branch in question of the lateral pterygoid muscle, with original enthesis including bone fragment, is secured on the prosthesis, on the porous area on the antero-medial side of the condylar neck.

17. The method according to claim 16, wherein prior to step b) being carried out:

the open spaces are provided with a growth factor promoting the production of bone tissue; and/or stem cells are introduced into the open spaces.

18. The method according to claim 16, wherein the size of the cross-section of the open spaces is in the range of 0.35 mm-1.0 mm.

\* \* \* \* \*